United States Patent [19]

Feldman

[11] Patent Number: 5,681,165
[45] Date of Patent: Oct. 28, 1997

[54] CERAMIC ORTHODONTIC BRACKET AND METHOD OF MANUFACTURING

[76] Inventor: Randy Mark Feldman, 8639 N. Himes, Apt. 3801, Tampa, Fla. 33614

[21] Appl. No.: 437,666

[22] Filed: May 9, 1995

[51] Int. Cl.[6] ................................................. A61C 3/00
[52] U.S. Cl. ................................................. 433/8
[58] Field of Search ........................... 433/8, 9, 13, 17, 433/11, 22, 14

[56] References Cited

U.S. PATENT DOCUMENTS

| | | | |
|---|---|---|---|
| 4,216,583 | 8/1980 | Reynolds | 433/9 |
| 4,219,617 | 8/1980 | Wallshein | 433/8 |
| 4,322,206 | 3/1982 | Reynolds | 433/9 |
| 4,878,840 | 11/1989 | Reynolds | 433/9 |
| 5,174,754 | 12/1992 | Meritt | 433/8 |
| 5,254,002 | 10/1993 | Reher et al. | 433/8 |
| 5,322,435 | 6/1994 | Pletcher | 433/8 |
| 5,429,499 | 7/1995 | Sernetz | 433/8 |
| 5,439,378 | 8/1995 | Damon | 433/8 |
| 5,439,379 | 8/1995 | Hansen | 433/8 |
| 5,441,408 | 8/1995 | Moschik | 433/8 |
| B1 4,216,583 | 3/1994 | Reynolds | 433/9 |

*Primary Examiner*—Cary E. O'Connor
*Attorney, Agent, or Firm*—Michael A. O'Neil; Russell N. Rippamonti

[57] ABSTRACT

A wide, shallow slot (60) is machined in the posterior surface (48) of a ceramic bracket (20). Thereafter a narrow, deep slot (70) is formed in the bracket (20). An elastomeric member (80) is positioned in the slot (70), and a plate (82) is secured in the slot (60) to close the slot (70). After the bracket (20) is mounted on the tooth (T) of a patient, the elastomeric member (80) is removed and is replaced by an appliance (A).

7 Claims, 3 Drawing Sheets

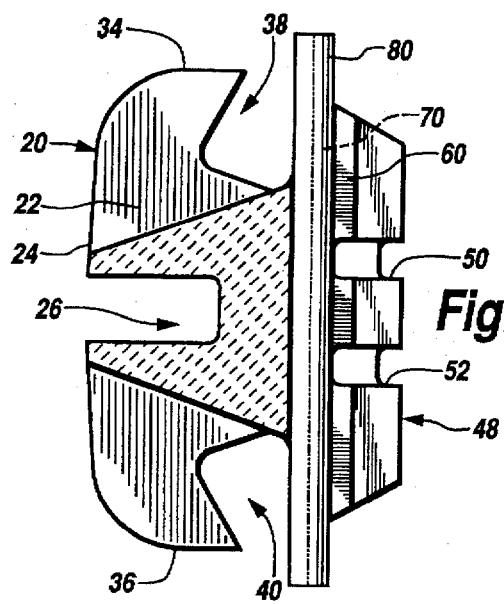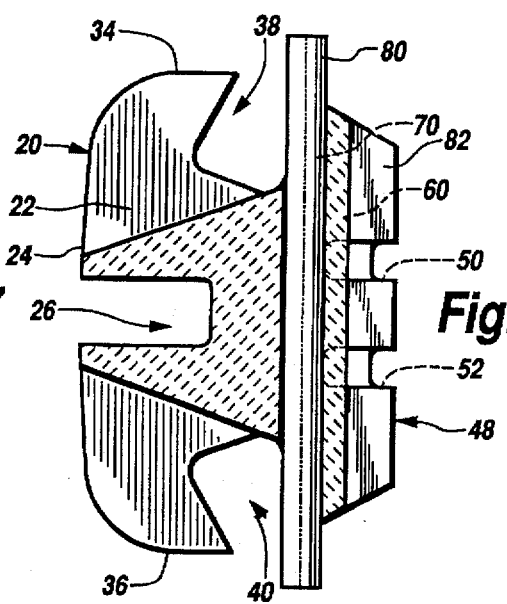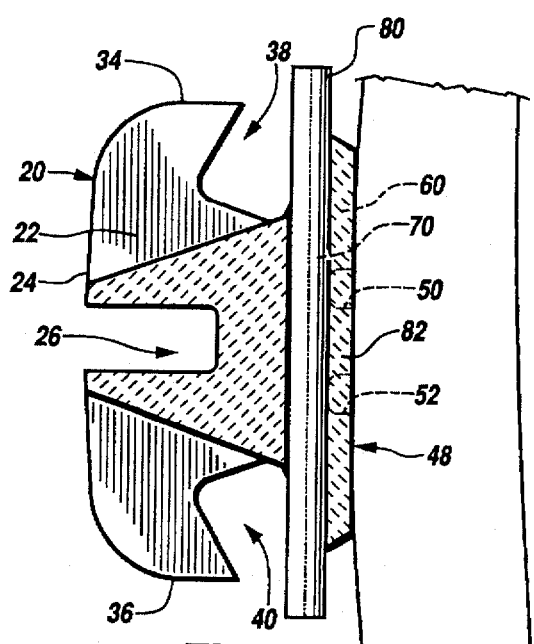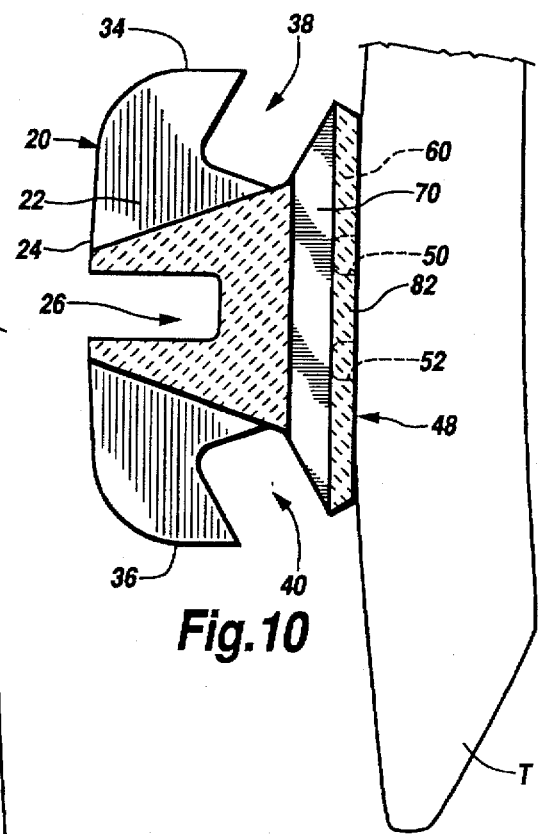

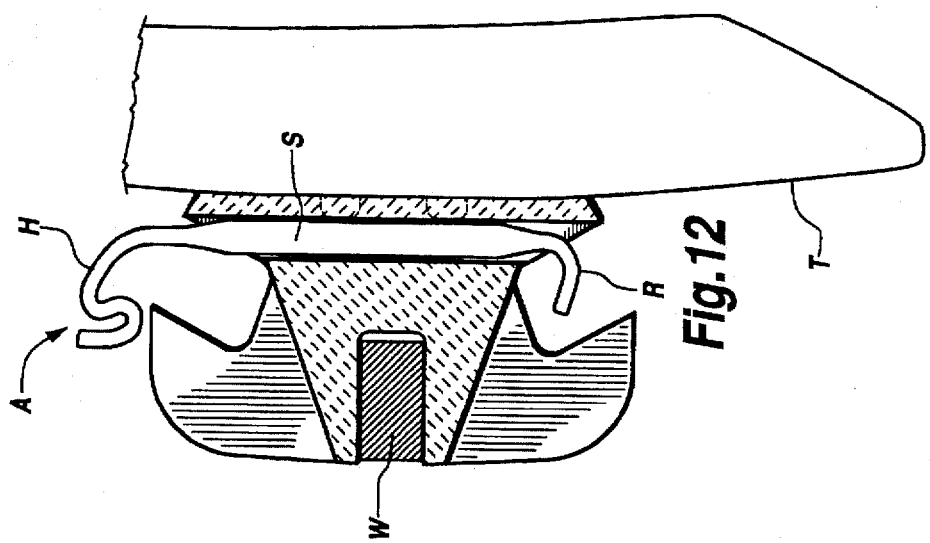
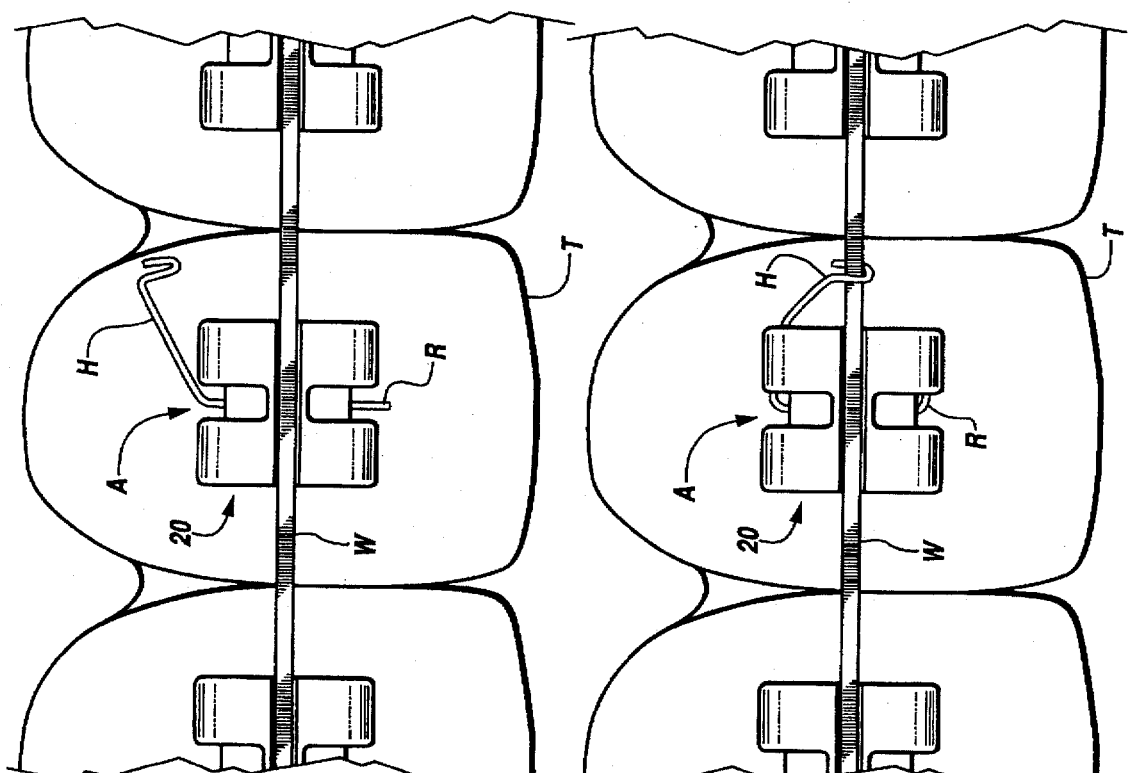

5,681,165

1

CERAMIC ORTHODONTIC BRACKET AND METHOD OF MANUFACTURING

TECHNICAL FIELD

This invention relates generally to ceramic orthodontic brackets, and more particularly to a ceramic orthodontic bracket adapted to receive, position, and retain selected orthodontic appliances, and to a method of manufacturing the bracket.

BACKGROUND OF THE INVENTION

In its broadest aspect, orthodontia comprises the repositioning of teeth by the selected application of tooth moving forces thereto. Traditionally, orthodontic brackets have been mounted on metal tooth-encircling bands. More recently, the practice of mounting orthodontic brackets directly on teeth has become widespread. In either case, tooth moving forces are generated by ligating orthodontic brackets secured to the teeth to be moved to archwires extending adjacent the anterior surfaces of the teeth.

Originally, orthodontic brackets were hand-wrought from precious metals. Later the use of brackets machined from stainless steel became almost universal. More recently, the use of ceramic orthodontic brackets has become well known. Ceramic orthodontic brackets are considered superior to stainless steel orthodontic brackets because they are more comfortable for the patient and considerably less noticeable in use.

In many instances it is considered desirable to employ various appliances in conjunction with orthodontic brackets during the orthodontic procedure. For example, appliances may be used to generate tooth moving forces which are not readily attained by conventional ligation techniques. Various ceramic orthodontic brackets adopted to receive, position, and retain selected appliances have been known and used in the past; however, it has not heretofore been possible to utilize appliances in conjunction with ceramic orthodontic brackets. In general this has been due to difficulties in machining orthodontic brackets after they are manufactured.

SUMMARY OF THE INVENTION

The present invention comprises a ceramic orthodontic bracket and its method of manufacture which overcomes the foregoing and other deficiencies long since known in the prior art. In accordance with the broader aspects of the invention, there is provided a method of adapting ceramic orthodontic brackets to receive, position, and retain orthodontic appliances. The invention further comprises ceramic orthodontic brackets manufactured in accordance with the method.

More particularly, in accordance with the invention a wide, shallow slot is first machined in the rear or posterior surface of an otherwise conventional ceramic bracket. Next, a narrow, deep slot is formed in the orthodontic bracket. Preferably, the narrow, deep slot is centered relative to the wide, shallow slot and extends inwardly therefrom.

The elastomeric member is next positioned in the narrow, deep slot. After the elastomeric member is positioned, a ceramic plate is secured in the wide, shallow slot, preferably by means of a suitable adhesive. By this means there is formed an enclosed appliance receiving slot which extends through the ceramic orthodontic bracket from the gingival surface to the incisal surface thereof.

The ceramic orthodontic bracket having the appliance receiving slot formed therein is delivered to the orthodontist or dentist with the ceramic plate secured in place in the wide, shallow slot and with the elastomeric member positioned in the appliance receiving slot. Preferably, the elastomeric member remains positioned in the appliance receiving slot while the orthodontist or dentist bonds the ceramic orthodontic appliance to the tooth of the patient utilizing conventional techniques. Thereafter, the elastomeric member is removed and a selected orthodontic appliance is extended through the appliance receiving slot of the ceramic orthodontic bracket. The appliance is positioned and retained in accordance using conventional techniques, and is thereafter utilized in the orthodontic procedure.

BRIEF DESCRIPTION OF THE DRAWINGS

A more complete understanding of the invention may be had by reference to the following Detailed Description when taken in conjunction with the accompanying Drawings, wherein:

FIG. 7 is a sectional view of the bracket of FIG. 6 illustrating a later step in the method of the invention;

FIG. 8 is a view similar to FIG. 7 illustrating the completion of the bracket of the invention;

FIG. 9 is an illustration of the bracket of the present invention secured to the tooth of a patient;

FIG. 10 is an illustration similar to FIG. 9 showing the bracket of the present invention conditioned to receive an orthodontic appliance therein;

FIG. 11 is an anterior view of the bracket of the present invention showing the bracket mounted on the tooth of a patient and having an orthodontic appliance positioned therein;

FIG. 12 is a view similar to FIG. 10 showing the bracket of the invention having an orthodontic appliance positioned and retained therein; and FIG. 13 is a view similar to FIG. 11 showing the bracket of the present invention and illustrating the orthodontic appliance in use.

DETAILED DESCRIPTION

Figure 1:
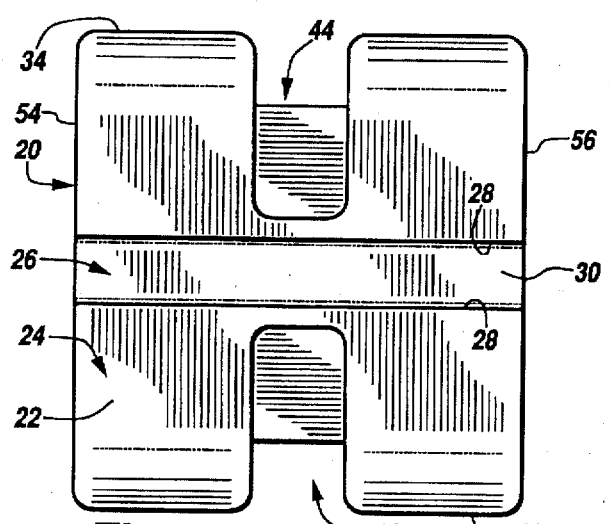
FIG. 1 is a front view of a conventional ceramic orthodontic bracket.
Figure 2:
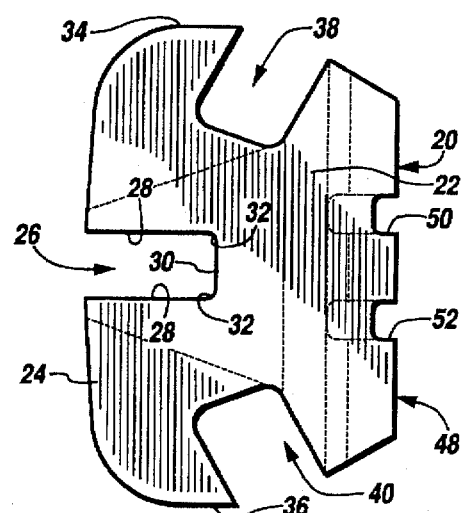
FIG. 2 is an end view of the bracket of FIG. 1.
Figure 3:
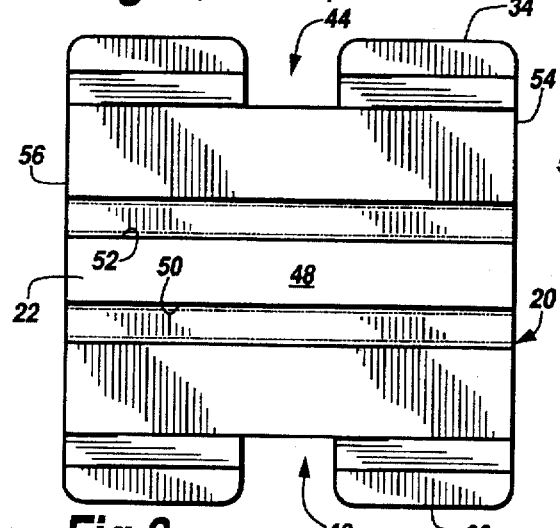
FIG. 3 is a rear view of the bracket of FIG. 1.

Referring now to the drawings, and particularly to FIGS. 1, 2 and 3 thereof, there is shown a ceramic orthodontic bracket 20. The bracket 20 may be formed entirely from a ceramic material such as alumina. Alternatively, the bracket 20 may be provided with one or more inserts formed from selected metals or other materials.

The bracket 20 comprises a unitary body 22. The body 22 comprises an anterior surface 24 which is domed. An archwire slot 26 is formed in the anterior surface 24 of the body 22 and comprises opposed sidewalls 28 in a bottom wall 30. The intersections 32 between the sidewalls 28 and the bottom wall 30 of the archwire slot 26 are rounded. Alternatively, the entire bottom wall 30 of the archwire 26 may comprise a rounded surface.

The body 22 of the bracket 20 further comprises an upper end 34 and a lower end 36. Ligating slots 38 and 40 are formed in the upper end 34 and the lower end 36 of the body 22, respectively. In the use of the bracket 20 the ligating slots 38 and 40 receive ligating members, typically tie wires or elastomeric bands, which are used in ligating the bracket 20 to an archwire extending through the archwire slot 26.

Referring particularly to FIG. 1, the anterior surface 24 of the body 22 of the bracket 20 is partially bisected by slot 44 extending downwardly from the upper surface 34 and a slot 46 extending upwardly from the lower surface 36. Thus, the bracket 20 comprises a so-called twin bracket, it being understood that the present invention is equally applicable to other conventional bracket types. As is true with other twin brackets, the slots 44 and 46 allow the bracket 20 to be ligated to an archwire extending through the archwire slot either on the left side, or on the right side, or on both sides of the bracket 20, depending on the requirements of a particular orthodontic procedure.

Referring to FIGS. 2 and 3, the body 22 of the bracket 20 further comprises a planar posterior surface 48. The posterior surface 48 is provided with a pair of slots 50 and 52 which extend transversely across the posterior surface 48 of the body 22 from the left side 54 to the right side 56 thereof. In the use of the bracket 20, the slots 50 and 52 are used to receive quantities of bonding material, whereby the attachment of the bracket 20 to a tooth is facilitated. Those skilled in the art will understand that other configurations of bonding material receiving cavities may be utilized in the posterior surface 48 of the body 22, if desired.

Figure 4:
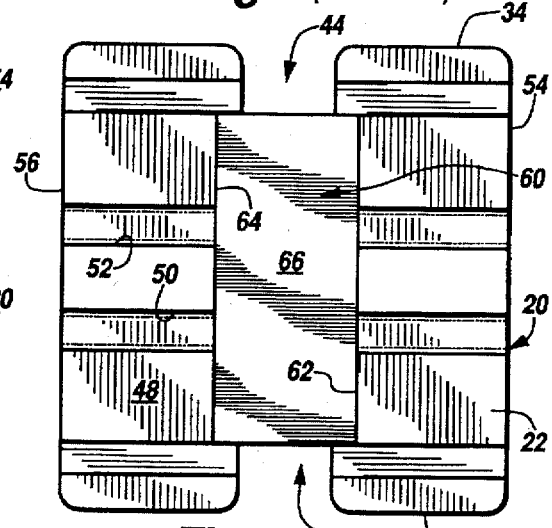
FIG. 4 is a view similar to FIG. 3 illustrating a first step in the method of the present invention.

The first step in the method of the present invention is illustrated in FIG. 4. A wide, shallow slot 60 is machined in the posterior surface 48 of the body 22 of the bracket 20 using a diamond cutting wheel. The slot 60 comprises a pair of sidewalls 62 and 64 each extending perpendicularly to the posterior surface 48 and parallel to the sidewalls 54 and 56 of the body 22 of the bracket 20. The slot 60 further comprises a bottom wall 66 which extends parallel to the posterior surface 48. The wide, shallow slot 60 is preferably centered between the sidewalls 54 and 56 of the body 22 of the bracket 20, however, other positioning of the slot 60 may be utilized in accordance with the requirements of particular applications of the invention.

Figure 5:
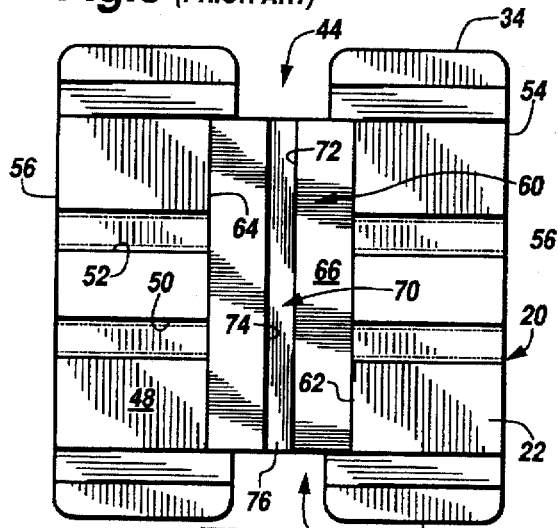
FIG. 5 is a view similar to FIG. 4 illustrating a second step in the method of the invention.

The next step in the method of the present invention is illustrated in FIG. 5. A narrow, deep slot 70 is machined in the body 22 of the bracket 20 and extends inwardly from the bottom wall 66 of the wide, shallow slot 60 using a diamond cutting wheel. The slot 70 comprises opposed sidewalls 72 and 74 which extend perpendicularly to the bottom wall 66 of the slot 60 and parallel to the sidewalls 62 and 64 thereof, and a bottom wall 76 which extends parallel to the bottom wall 66 of the slot 60. The narrow, deep slot 70 is preferably centered between the sidewalls 62 and 64 of the slot 60, and between the sidewalls 54 and 56 of the body 22, however, other spatial arrangements between the narrow, deep slot 70, the wide, shallow slot 60 and the other structural components of the bracket 20 may be employed in accordance with the requirements of particular applications of the invention.

Figure 6:
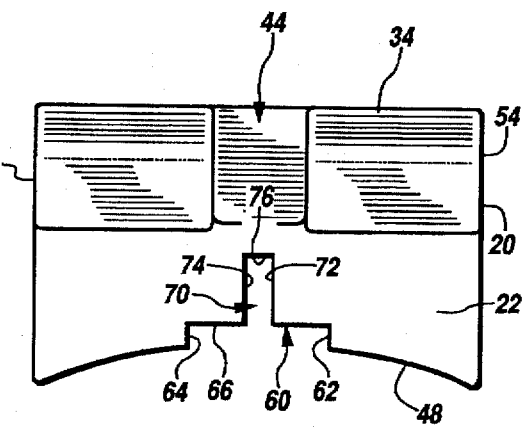
FIG. 6 is a top view of the bracket illustrating the results of the steps shown in FIGS. 4 and 5.

The results of the steps illustrated in FIGS. 4 and 5 are further illustrated in FIG. 6. The wide, shallow slot 60 is formed in the posterior wall 48 of the body 22 of the bracket 20 and comprises spaced, parallel sidewalls 62 and 64 and a bottom wall 66 extending perpendicularly to the sidewalls. The narrow, deep slot 70 comprises sidewalls 72 and 74 extending parallel to the sidewall 62 and 64 of the wide, shallow slot 60 and perpendicularly to the bottom wall 66 thereof. The slot 70 further comprises a bottom wall 76 which extends parallel to the bottom wall 66 of the slot 60.

It is important in the practice of the invention that the sidewalls 62 and 64 are square, i.e., perpendicular, relative to the bottom wall 66, and the sidewalls 72 and 74 and square related to the bottom wall 76.

Referring now to FIG. 7, the next step in the method of the present invention comprises the positioning of an elastomeric member 80 in the narrow, deep slot 70 previously formed in the body 22 of the bracket 20. The elastomeric member 80 may comprise a length of elastomeric tubing formed from rubber, plastic or any other suitable elastomeric material dimensioned to completely fill the narrow, deep slot 70 when compressed therein. Other configurations comprising the elastomeric member 80 may be employed in the practice of the invention provided only that the elastomeric member 80 is sufficiently pliant to completely fill the slot 70 when compressed therein and sufficiently strong to facilitate its removal subsequently in the practice of the method of the invention.

Referring to FIG. 8, the next step in the method of the present invention comprises the mounting of a plate 82 in the wide, shallow slot 60 formed in the body 22 of the bracket 20. The positioning of the plate 82 in the slot 60 compresses the elastomeric member 80 somewhat in the narrow, deep slot 70 and temporarily retains the elastomeric member 80 in the slot 70. The plate 82 has dimensions identical to those of the wide, shallow slot 60 formed in the body 22 of the bracket 20. The plate 82 is preferably formed from a ceramic material such as alumina, however, it will be understood that other materials may be used in the fabrication of the plate 82, if desired.

Prior to the mounting of the plate 82 in the wide, shallow slot 60, both the bracket 20 and the plate 82 are cleaned using a conventional solvent, such as carbon tetrachloride. Mounting of the plate 82 in the slot 60 is facilitated by treating both the bracket 20 and the plate 82 with a conventional saline solution, preferably at an elevated temperature, for example 125° F.

The plate 82 is permanently secured in the wide, shallow slot 60 by means of a suitable adhesive. Preferably, the plate 82 is secured in the slot 60 using Reliance Light-Bond Adhesive, with the paste and the sealant thereof being mixed to a thick consistency. Using a fine paint brush, the adhesive is spread on the sidewall 62 and 64 and the bottom wall 66 of the slot 60. The plate 82 is then placed in the slot 60, and is held in place under light pressure using tweezers. A light gun is actuated for approximately twenty seconds to initially set the adhesive. Thereafter the bracket 20 having the plate 82 positioned in the slot 60 is exposed to direct sunlight or to ultra violet light for approximately 30 minutes to fully set the adhesive.

The mounting of the plate 82 in the wide, shallow slot 60 completely fills the slot 60 and closes the previously open posterior end of the deep, narrow slot 70. In this matter, the slot 70 is reconfigured from an open-sided slot into an appliance receiving slot which is closed on all four sides but which is open at the top and bottom ends thereof and which extends entirely through the body 22 of the bracket 20 in a direction substantially parallel to the anterior surface 24 and the posterior surface 48 thereof. It will be understood that at this stage in the practice of the invention, the slot 70 is completely filled by the elastomeric member 80.

Referring now to FIG. 9, the bracket 20 having the elastomeric member 80 filling the slot 70 and the plate 82 filling the slot 60 is mounted on the tooth T of a patient. The mounting of the bracket 20 on the tooth T is conventional in nature and utilizes a conventional bonding material which is applied to the posterior surface 48 of the bracket 20. Quantities of the bonding material are received in the slots 50 and 52 formed in the posterior surface 48 of the bracket 20 to facilitate the bonding thereof to the tooth T. Those skilled in the art will appreciate the fact that the primary purpose of utilizing the elastomeric member 80 to fill the slot 70 is to prevent the adhesive which is used to secure the plate 82 in the slot 60 and to prevent the bonding material which is utilized to secure the bracket 20 to the tooth T from entering the slot 70. Thus, the slot 70 remains entirely free of contamination throughout the plate mounting and bracket bonding procedures.

Referring now to FIGS. 10, 11, 12 and 13, the next step in the practice of the present invention comprises the removal of the elastomeric member 80 from the slot 70. Such removal may be accomplished utilizing conventional orthodontic or other dental pliers to grasp a convenient end of the elastomeric member 80, where upon an endwise directed force is applied to the elastomeric member 80 to withdraw it from the slot 70. Upon removal of the elastomeric member 80 from the slot 70, an appliance A may be installed therein. Although a particular orthodontic appliance A is illustrated in the Drawings, it will be understood that the present invention is equally adopted for use with various other conventional orthodontic appliances in accordance with the requirements of a particular orthodontic procedure.

As is best shown in FIG. 12, the orthodontic appliance may comprise a hook end H extending to a shank S which in turn extends to a retaining end R. Preferably, the dimensions of the slot 70, upon closure by the plate 82, are closely matched to the dimensions of the shank S of the appliance A whereby the slot 70 functions to position and locate the appliance A relative to the bracket 20. After the appliance A is positioned in the slot 70, the retaining end R thereof may be bent into engagement with a bracket 20 utilizing conventional orthodontic instruments and procedures, whereby the appliance A is retained in the slot 70. Thereafter the hook end H of the appliance A may be engaged with an archwire W extending through the archwire slot 26 of the bracket 20 to facilitate the desired movement of the tooth T in accordance with the orthodontic procedure then underway.

Those skilled in the art will understand that the present invention comprises a method for providing an appliance receiving, positioning and retaining slot in a ceramic orthodontic bracket. The method of the invention may be utilized in conjunction with various conventional bracket types and is not limited to use with the twin bracket illustrated in the Drawings. The invention further comprises a ceramic bracket having an appliance receiving, positioning and retaining slot, whereby conventional orthodontic appliances may be utilized in conjunction with ceramic orthodontic brackets in a manner similar to the use of such appliances in conjunction with brackets formed from stainless steel and other metals.

Although preferred embodiments of the invention have been illustrated in the accompanying Drawings and described in the foregoing Detailed Description, it will be understood that the invention is not limited to the embodiments disclosed, but is capable of numerous rearrangements, modifications, and variations of the parts and elements in accordance with the spirit of the invention.

I claim:

1. An orthodontic bracket for use on a tooth comprising:
   a body formed from a ceramic material and having an anterior surface, a posterior surface, a first surface to be oriented proximal to a gingival surface of the tooth on which the bracket is to be affixed, a second surface to be oriented proximal to the incisal or occlusal surface of the tooth on which the bracket is to be affixed, and a pair of opposed sides;
   an appliance receiving slot extending from the first surface of the bracket to the second surface of the bracket, and open to the posterior surface of the bracket, said slot including:
      a first narrow, deep slot open to the posterior surface of the bracket, and said first slot having a pair of opposed parallel sidewalls extending parallel to the opposed sides of the bracket, and a bottom wall extending perpendicular to the opposed sidewalls;
      a second wide, shallow slot extending outwardly from the opposed sidewalls of the first slot and open to the posterior surface of the bracket, said second slot having a pair of opposed sidewalls extending parallel to the opposed sides of the bracket; and
   an elastomeric member located in the first narrow deep slot.

2. An orthodontic bracket for use on a tooth comprising:
   a body formed from a ceramic material and having an anterior surface, a posterior surface, a first surface to be oriented proximal to a gingival surface of the tooth on which the bracket is to be affixed, a second surface to be oriented proximal to the incisal or occlusal surface of the tooth on which the bracket is to be affixed, and a pair of opposed sides;
   an appliance receiving slot extending from the first surface of the bracket to the second surface of the bracket, and open to the posterior surface of the bracket, said slot including:
      a first narrow, deep slot open to the posterior surface of the bracket, and said first slot having a pair of opposed parallel sidewalls extending parallel to the opposed sides of the bracket, and a bottom wall extending perpendicular to the opposed sidewalls;
      a second wide, shallow slot extending outwardly from the opposed sidewalls of the first slot and open to the posterior surface of the bracket, said second slot having a pair of opposed sidewalls extending parallel to the opposed sides of the bracket; and
   a plate located in the second wide slot forming a portion of the posterior surface of the body of the orthodontic bracket and closing an open side of the appliance receiving slot opposite the bottom wall of the first narrow slot.

3. An orthodontic bracket for use on a tooth comprising:
   a body formed from a ceramic material and having an anterior surface, a posterior surface, a first surface to be oriented proximal to a gingival surface of the tooth on which the bracket is to be affixed, a second surface to be oriented proximal to the incisal or occlusal surface of the tooth on which the bracket is to be affixed, and a pair of opposed sides; and
   an appliance receiving slot extending from the first surface of the bracket to the second surface of the bracket, and open to the posterior surface of the bracket, said slot including:
      a first narrow, deep slot open to the posterior surface of the bracket, said first slot having:
         a pair of opposed parallel sidewalls extending parallel to the opposed sides of the bracket and perpendicular to the posterior surface of the bracket, and a bottom wall interconnecting the sidewalls and extending parallel to the posterior surface of the orthodontic bracket, and a second wide, shallow slot extending outwardly from the opposed sidewalls of the first slot and open to the posterior surface of the bracket, said second slot having:

a pair of opposed sidewalls extending parallel to the opposed sides of the bracket and perpendicular to the posterior surface of the bracket, and a bottom wall extending perpendicular to the opposed sidewalls and extending parallel to the posterior surface of the orthodontic bracket; and an elastomeric member located in the first narrow slot; and a plate located in the second wide slot forming a portion of the posterior surface of the body of the orthodontic bracket and closing an open side of the appliance receiving slot opposite the bottom wall of the second narrow slot.

4. A method of forming an appliance receiving slot in a ceramic orthodontic bracket comprising the steps of:

providing a body formed from a ceramic material and having an anterior surface, a posterior surface, a first surface to be oriented proximal to a gingival surface of tooth on which the bracket is to be affixed, a second surface to be oriented proximal to the incisal or occlusal surface of the tooth on which the bracket is to be affixed, and a pair of opposed sides;

forming a first wide, shallow slot extending from the first surface of the bracket to the second surface of the bracket, and open to the posterior surface of the bracket, said second slot having:

a pair of opposed sidewalls extending parallel to the opposed sides of the bracket and a bottom wall extending perpendicular to the opposed sidewalls and extending parallel to the posterior surface of the orthodontic bracket;

forming a second narrow, deep slot positioned between the opposed sidewalls of the first wide slot and extending from the first surface of the bracket to the second surface of the bracket, and open to the posterior surface of the bracket, said first slot having:

a pair of opposed parallel sidewalls extending parallel to the opposed sides of the bracket and a bottom wall interconnecting the sidewalls and extending parallel to the posterior surface of the orthodontic bracket; and installing a elastomeric member in the second narrow slot.

5. A method of forming an appliance receiving slot in a ceramic orthodontic bracket comprising the steps of:

providing a body formed from a ceramic material and having an anterior surface, a posterior surface, a first surface to be oriented proximal to a gingival surface of tooth on which the bracket is to be affixed, a second surface to be oriented proximal to the incisal or occlusal surface of the tooth on which the bracket is to be affixed, and a pair of opposed sides;

forming a first wide, shallow slot extending from the first surface of the bracket to the second surface of the bracket, and open to the posterior surface of the bracket, said second slot having:

a pair of opposed sidewalls extending parallel to the opposed sides of the bracket and a bottom wall extending perpendicular to the opposed sidewalls and extending parallel to the posterior surface of the orthodontic bracket;

forming a second narrow, deep slot positioned between the opposed sidewalls of the first wide slot and extending from the first surface of the bracket to the second surface of the bracket, and open to the posterior surface of the bracket, said first slot having:

a pair of opposed parallel sidewalls extending parallel to the opposed sides of the bracket and a bottom wall interconnecting the sidewalls and extending parallel to the posterior surface of the orthodontic bracket; and securing a plate in the first wide, shallow slot and thereby closing an open side of the second narrow, deep slot formed in the orthodontic bracket.

6. A method of forming an appliance receiving slot in a ceramic orthodontic bracket comprising the steps of:

providing a body formed from a ceramic material and having an anterior surface, a posterior surface, a first surface to be oriented proximal to a gingival surface of tooth on which the bracket is to be affixed, a second surface to be oriented proximal to the incisal or occlusal surface of the tooth on which the bracket is to be affixed, and a pair of opposed sides;

forming an appliance receiving slot extending from the first surface of the bracket to the second surface of the bracket, and open to the posterior surface of the bracket, said step for forming an appliance receiving slot further including the steps:

forming a first narrow, deep slot open to the posterior surface of the bracket, said first slot having:

a pair of opposed parallel sidewalls extending parallel to the opposed sides of the bracket and perpendicular to the posterior surface of the bracket, and a bottom wall extending perpendicular to the opposed sidewalls and extending parallel to the posterior surface of the orthodontic bracket; and forming a second wide, shallow slot extending outwardly from the opposed sidewalls of the first slot and open to the posterior surface of the bracket, said second slot having:

a pair of opposed sidewalls extending parallel to the opposed sides of the bracket and perpendicular to the posterior surface of the bracket, and a bottom wall interconnecting the sidewalls and extending parallel to the posterior surface of the orthodontic bracket; and installing an elastomeric member in the first narrow slot.

7. A method of forming an appliance receiving slot in a ceramic orthodontic bracket comprising the steps of:

providing a body formed from a ceramic material and having an anterior surface, a posterior surface, a first surface to be oriented proximal to a gingival surface of tooth on which the bracket is to be affixed, a second surface to be oriented proximal to the incisal or occlusal surface of the tooth on which the bracket is to be affixed, and a pair of opposed sides;

forming an appliance receiving slot extending from the first surface of the bracket to the second surface of the bracket, and open to the posterior surface of the bracket, said step for forming an appliance receiving slot further including the steps:

forming a first narrow, deep slot open to the posterior surface of the bracket, said first slot having:
- a pair of opposed parallel sidewalls extending parallel to the opposed sides of the bracket and perpendicular to the posterior surface of the bracket, and
- a bottom wall extending perpendicular to the opposed sidewalls and extending parallel to the posterior surface of the orthodontic bracket; and forming a second wide, shallow slot extending outwardly from the opposed sidewalls of the first slot and open to the posterior surface of the bracket, said second slot having:
- a pair of opposed sidewalls extending parallel to the opposed sides of the bracket and perpendicular to the posterior surface of the bracket, and
- a bottom wall interconnecting the sidewalls and extending parallel to the posterior surface of the orthodontic bracket; and securing a plate in the second wide, shallow slot and thereby closing an open side of the first narrow, deep slot formed in the orthodontic bracket.

* * * * *